United States Patent
Shah et al.

(10) Patent No.: US 11,013,501 B2
(45) Date of Patent: May 25, 2021

(54) METHOD OF PROTECTING THE PERITONEUM AGAINST TEARING AND OTHER INJURY BEFORE AN ACTIVE SURGICAL INTERVENTION AT OR NEAR THE PERITONEUM

(71) Applicant: Davol, Inc., Warwick, RI (US)

(72) Inventors: Devang Vijay Shah, Franklin, MA (US); Robert Richard, Wakefield, RI (US); Christopher Bowley, Newport, RI (US)

(73) Assignee: Davol, Inc., Warwick, RI (US)

(*) Notice: Subject to any disclaimer, the term of this patent is extended or adjusted under 35 U.S.C. 154(b) by 138 days.

(21) Appl. No.: 16/210,442

(22) Filed: Dec. 5, 2018

(65) Prior Publication Data

US 2019/0175161 A1    Jun. 13, 2019

Related U.S. Application Data

(60) Provisional application No. 62/596,750, filed on Dec. 8, 2017.

(51) Int. Cl.
 *A61B 17/00* (2006.01)
 *A61F 2/00* (2006.01)
 (Continued)

(52) U.S. Cl.
 CPC ........ *A61B 17/00234* (2013.01); *A61B 90/04* (2016.02); *A61F 2/0063* (2013.01);
 (Continued)

(58) Field of Classification Search
 CPC .......... A61B 17/00234; A61B 17/0281; A61B 2017/00522; A61B 2017/00557; A61B 2017/00951; A61B 2017/00995; A61B 2017/0225; A61B 2090/0427; A61B 90/04; A61B 17/0218; A61B 17/0239; A61B 2017/0287; A61B 2017/0212; A61B 90/02; A61B 90/03; A61B 2090/033; A61B 2090/036; A61B 2090/0409;
 (Continued)

(56) References Cited

U.S. PATENT DOCUMENTS 5,836,871 A * 11/1998 Wallace ............. A61B 17/0218
                                                     600/204
5,865,728 A *  2/1999 Moll .................. A61B 17/0218
                                                     600/204

(Continued)

OTHER PUBLICATIONS

[No Author Listed] Your Choice of Sealant Matters: Seal to Heal. DuraSeal® Dural Sealant System. Integra. Publicly available before Dec. 8, 2017. 3 pages.

*Primary Examiner* — Tan-Uyen T Ho
*Assistant Examiner* — Chima U Igboko
(74) *Attorney, Agent, or Firm* — Wolf, Greenfield & Sacks, P.C.

(57) ABSTRACT

Methods for protecting a peritoneum or other tissue during a surgical procedure are disclosed. In some embodiments, a protective lining is applied to the peritoneum or other tissue before an active surgical intervention, such as before tissue dissection, tissue approximation, and/or other surgical act. In some embodiments, the protective lining includes a protective film applied to the peritoneum or other tissue via a delivery balloon or via a spray instrument.

34 Claims, 7 Drawing Sheets

(51) Int. Cl.
*A61B 90/00* (2016.01)
*A61M 39/02* (2006.01)
*A61B 17/02* (2006.01)

(52) U.S. Cl.
CPC . *A61B 17/0281* (2013.01); *A61B 2017/00522* (2013.01); *A61B 2017/00557* (2013.01); *A61B 2017/00951* (2013.01); *A61B 2017/00995* (2013.01); *A61B 2017/0225* (2013.01); *A61B 2090/0427* (2016.02); *A61F 2002/0072* (2013.01); *A61M 39/0247* (2013.01); *A61M 2039/0279* (2013.01)

(58) Field of Classification Search
CPC ..... A61B 2090/0418; A61F 2002/0072; A61F 2/0063; A61M 2039/0279; A61M 39/0247; A61M 2039/0285; A61M 2039/0288; A61M 2039/0294; A61M 2039/0297
See application file for complete search history.

(56) References Cited

U.S. PATENT DOCUMENTS

| | | | |
|---|---|---|---|
| 6,632,234 | B2 | 10/2003 | Kieturakis et al. |
| 9,649,331 | B2 | 5/2017 | Eaton et al. |
| 2010/0305589 | A1* | 12/2010 | Solecki ............... A61L 24/0042 606/151 |
| 2011/0270286 | A1* | 11/2011 | Keane ................. A61L 31/129 606/151 |
| 2012/0078227 | A1 | 3/2012 | Kangas |
| 2014/0243395 | A1 | 8/2014 | Rudolph et al. |
| 2014/0309497 | A1* | 10/2014 | Solomon ................ A61B 46/10 600/202 |
| 2016/0166368 | A1* | 6/2016 | Solecki ................ A61F 2/0063 606/151 |

* cited by examiner

METHOD OF PROTECTING THE PERITONEUM AGAINST TEARING AND OTHER INJURY BEFORE AN ACTIVE SURGICAL INTERVENTION AT OR NEAR THE PERITONEUM

CROSS-REFERENCE TO RELATED APPLICATIONS

This application claims the benefit under 35 U.S.C. § 119(e) to U.S. Provisional Application Ser. No. 62/596,750, entitled "METHOD OF PROTECTING THE PERITONEUM AGAINST TEARING AND OTHER INJURY BEFORE AN ACTIVE SURGICAL INTERVENTION AT OR NEAR THE PERITONEUM" and filed on Dec. 8, 2017, the entirety of which is herein incorporated by reference.

FIELD

The invention relates to methods of protecting the peritoneum against tearing and other injury before an active surgical intervention at or near the peritoneum.

BACKGROUND

The peritoneum is a relatively flimsy lining of the abdominal cavity that is susceptible to inadvertent tearing and other injury during a surgical procedure in the abdominal cavity and/or through the abdominal wall. It is known to apply a film-type barrier to the peritoneum to prevent formation of post-operative surgical adhesions, but such film-type barriers are applied only after the surgical intervention.

SUMMARY

According to one embodiment, a method of applying a protective lining to a peritoneum is disclosed. The method includes elevating an abdominal wall including a peritoneum away from viscera to create a working space, performing an active surgical intervention involving the created working space, and prior to the act of performing an active surgical intervention, applying a protective lining to at least a portion of the peritoneum in the working space.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF INVENTION

Figure 1A:
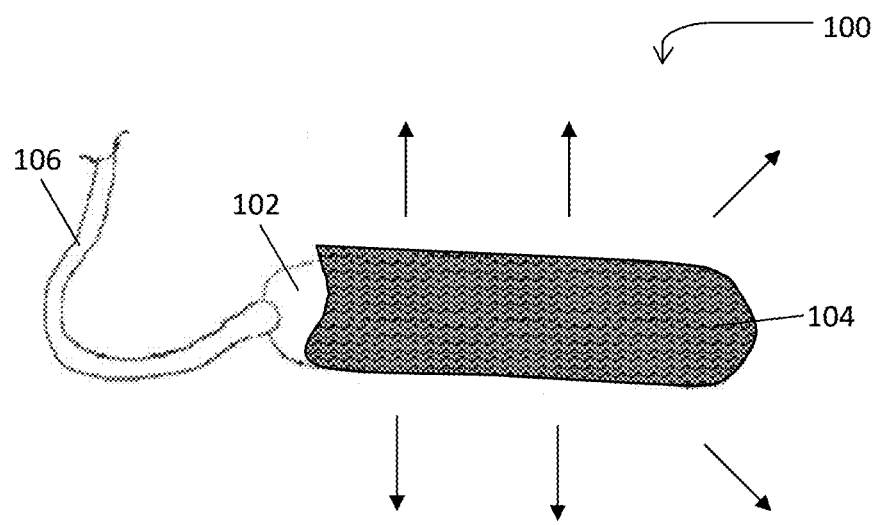
FIGS. 1A and 1B illustrate an expandable device for delivering a protective lining to a peritoneum according to an embodiment of the present disclosure, with a delivery balloon in a deflated and inflated configuration, respectively.

In various minimally invasive surgical procedures involving the abdominal cavity, the abdominal wall, including the peritoneum, is first elevated away from the viscera (e.g., intestine, liver, stomach) before any active surgical steps are performed. For example, in a laparoscopic or robotic-assisted repair of an abdominal wall hernia, an insufflating gas may be introduced into the abdominal cavity to lift the abdominal wall away from the bowel and create a working space in which to conduct the surgical intervention. Once the abdominal wall has been elevated, the protruding sac may be returned to its proper location and the weakness in the abdominal wall may be repaired, such as by placement of a mesh type prosthetic device over, under, and/or within the abdominal wall defect. Cholecystectomy (gall bladder removal), appendectomy (appendix removal), splenectomy (spleen removal), and nephrectomy (kidney removal), are representative of other conventional minimally invasive procedures that take place in the abdominal cavity after elevation of the abdominal wall away from the viscera.

During certain minimally invasive surgical procedures, such as those addressing an abdominal wall hernia (e.g., inguinal, femoral, incisional/ventral), active surgical intervention at or through the peritoneum may be required. End effectors of laparoscopic or robotic-assisted surgical instruments such as graspers, dissectors, cauterizers, staplers, and suture appliers, to name but a few, may be deployed from within the abdominal cavity to work directly on the peritoneum, and/or to pass through an opening in the peritoneum to reach the repair site. Such a peritoneal opening may have to be surgically formed or, if already present, may have to be enlarged by cutting or otherwise manipulating the peritoneum to allow the end effectors to reach the hernia in a preperitoneal repair. In certain minimally invasive procedures of the abdominal cavity, edges defining an opening of an expanded peritoneum may be grasped and manipulated to approximate the peritoneum. The peritoneum also may need to be manipulated to prepare the abdominal wall for placement of a prosthetic repair mesh such as in an intraperitoneal repair.

In any of these surgical applications, as well as in other minimally invasive procedures in the abdominal cavity, the peritoneum may be susceptible to inadvertent tearing, shredding or other damage by application of the end effectors of the surgical instruments. For example, injury to the peritoneum may occur when incising, manipulating or approximating the peritoneum. As another example, as surgical instruments are wielded within an expanded abdominal cavity that is defined by an elevated peritoneum, the end effectors may inadvertently come into contact with this vulnerable abdominal wall lining, potentially leading to tearing, shredding or other damage thereof. As will be appreciated, in such an example, injury to the peritoneum may occur even during procedures that do not require manipulating and/or incising of the peritoneum. For example, surgical instruments may be wielded within and come into contact with the elevated peritoneum during a laparoscopic or robotic-assisted cholecystectomy, which ordinarily does not require manipulation or incision of the peritoneum.

The inventors have recognized that advantages may be realized by prophylactically providing a protective lining to at least certain portions of the peritoneum that may be exposed to surgical instruments before surgical intervention in the abdominal cavity. The protective lining may be applied to the peritoneum before elevation of the abdominal wall away from the viscera or may be applied to the peritoneum after such elevation but before intervention with laparoscopic or robotically-assisted surgical instruments that potentially could lead to tearing, shredding or other harm to the fragile abdominal wall lining. For example, the protective lining may be applied prior to dissection or approximation of the peritoneum, or prior to introduction of surgical instruments through the peritoneum into the preperitoneal space, or prior to application of surgical instruments in the intraperitoneal space, as the case may be.

In some embodiments, the protective lining may prophylactically prevent shredding or other injury to the peritoneum during a surgical procedure. For example, the protective lining may protect and/or preserve the fidelity of the peritoneum during dissection and/or ensure desired approximation of the tissue. The protective lining also may add stability to the peritoneum and thus aid in approximating the peritoneum, fixating an approximated peritoneum, and/or fixating a prosthesis to the peritoneum. Further, the protective lining may facilitate incision formation through the peritoneum that does not lead to tearing, shredding or other damage to portions of the peritoneum neighboring such an incision. The protective lining also may facilitate closure of the peritoneum. Additionally, the protective lining may minimize or prevent post-operative adhesion involving the peritoneum.

In some embodiments, the protective lining is arranged to increase the strength and/or integrity of the peritoneum. For example, the protective lining may facilitate approximation of the peritoneum, incising of the peritoneum, fixation of a repair device to the peritoneum, as well as atraumatic contact with the end effectors of one or more surgical instruments.

In some embodiments, the protective lining is permanent while in other embodiments it may be degradable over time. Thus, the lining may be arranged to degrade after a desired number of minutes, hours, days, or months after the surgery. In still other embodiments, the protective lining may be removed after completion of the surgical procedure.

In some embodiments, the protective lining is a preformed film that is transferrable to the peritoneum. For example, the transferrable film may be disposed on a delivery balloon or other expandable delivery device which, upon expansion, moves the lining against the peritoneum. The film itself may be tacky or may further include an adhesive to allow attachment to the peritoneum when the lining is against the peritoneum. In certain embodiments, fixation devices such as sutures, tacks, and the like, may be deployed to unite the film with the peritoneum. In other embodiments, a film is sprayed directly onto the peritoneum. Preferably, the film is flexible and movable with the peritoneum so as to cause minimal if any discomfort post-surgery if the lining remains within the patient. In some embodiments, the film is arranged to resemble native peritoneum tissue.

Figure 1B:
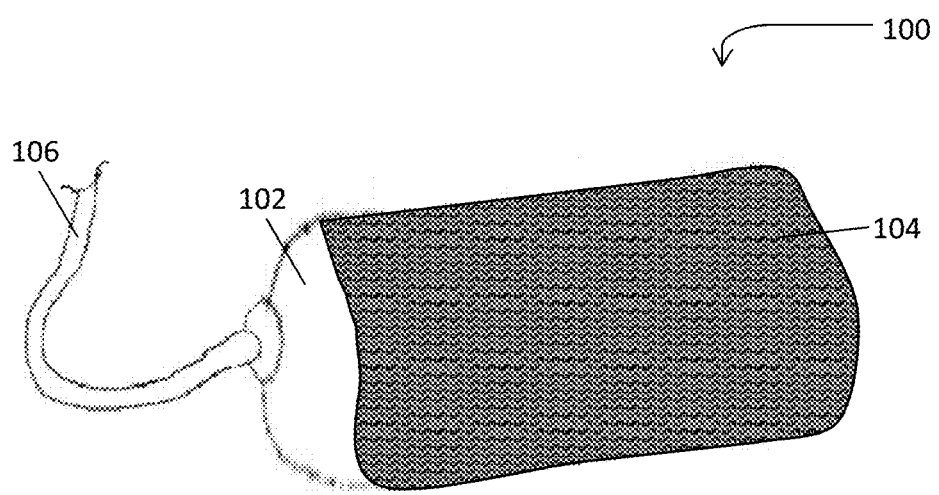

Turning now to the figures, FIGS. 1A and 1B illustrate an example of a protective lining delivery assembly 100 including an inflatable balloon 102 and a transferable film 104 disposed on the balloon 102. As shown, the transferable film may be disposed on an outer surface of the balloon, although the assembly is not so limited. In some embodiments, the balloon includes a conduit 106 through which an inflation fluid, such as air, $CO_2$, saline or another suitable fluid, is supplied and removed to inflate and deflate the balloon. Other approaches for expandably deploying a protective lining are contemplated and should be apparent to one of skill in the art.

Alternatively, a preformed film may otherwise be provided in the abdominal cavity and then positioned against the peritoneum. For example, a rolled up film may be delivered through a cannula into an expanded abdominal cavity. In such an example, a grasper or other tool may be used to unroll the film and position the protective lining against the peritoneum, such as for attachment.

In some embodiments, the transferrable film 104 includes an adhesive arranged to attach the film to the peritoneum when the film is positioned against the peritoneum, such as when the balloon is inflated. In some embodiments, the adhesive is moisture activated such that the film is attachable to the peritoneum when the film makes contact with the tissue. In other embodiments, the film may be activated, such as photo-activated, to cause the film to adhere to the peritoneum. The film also may include other constituents or otherwise be configured to allow the film to join to the peritoneum. For example, the film may include one or more clips or tacks to allow the film to join to the peritoneum.

Figure 2:
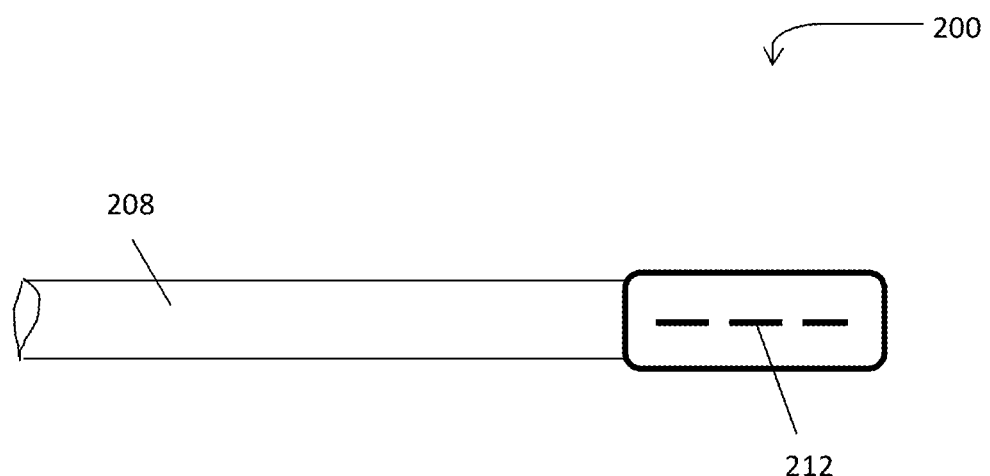
FIG. 2 is a view of an instrument for administering a protective lining to a peritoneum according to another embodiment of the present disclosure.

FIG. 2 illustrates another assembly 200 for delivering a protective lining to the peritoneum. As shown in this figure, the film delivery assembly 200 includes an instrument having an outlet for spraying a film on the peritoneum. A portion of the instrument may include a spray nozzle 208 with one or more openings 212 through which the film may be delivered. The nozzle may be located in a distal portion of the instrument or at any other portion that may be positionable relative to the peritoneum for spray application of the protective lining. For example, the nozzle may be integrated into the trocar in some embodiments. Various arrangements for spraying a protective lining onto a peritoneum are contemplated as should be apparent to one of skill in the art.

Figure 3A:
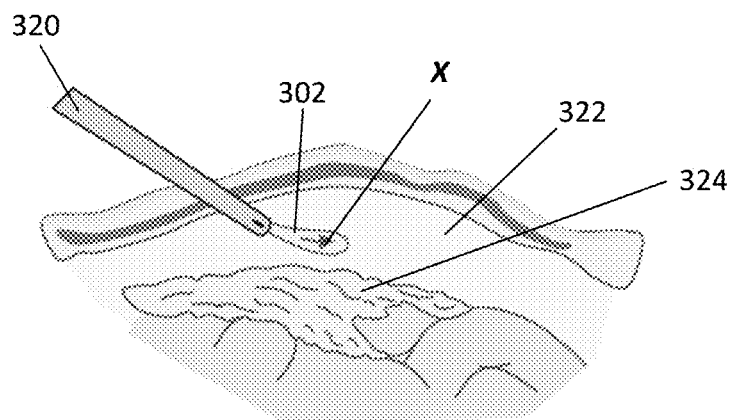
FIGS. 3A-3C illustrate a method of applying a protective lining to a peritoneum according to one embodiment.
Figure 3B:
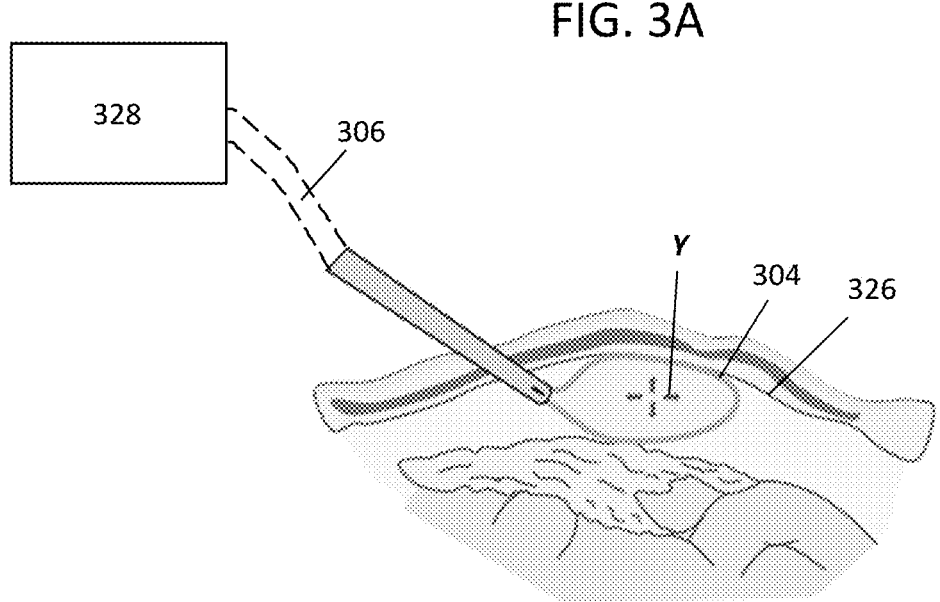
Figure 3C:
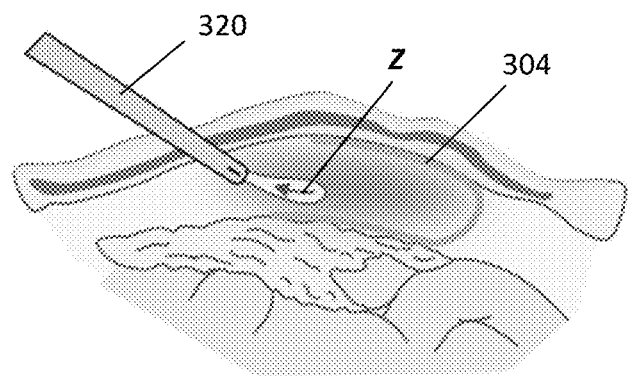

FIGS. 3A-3C illustrate a method of applying a protective lining to at least a portion of a peritoneum. As shown in these figures, the abdominal cavity, including the innermost peritoneal lining, has been elevated away from the viscera, for example by introduction of an insufflation gas, to create a working space. A cannula 320 extends from outside of the patient through the insufflated abdominal wall into the abdominal cavity 322. A deflated balloon 302 with a preformed, transferrable film is introduced into the expanded body cavity via the cannula (see arrow X). As shown in FIG. 3B, the balloon is inflatable via an inflating/deflating means 328 that is coupled to the balloon, such as via a conduit 306. For example, the inflating/deflating means 328 may supply the inflation fluid to the balloon via the conduit 306 to inflate the balloon.

In some embodiments, the balloon 302 is inflated (see arrows Y) until the film 304 makes contact with the peritoneum 326. The transferable film may be inherently tacky, include an adhesive, or otherwise be composed so as to adhere to the peritoneum. Alternatively, the film may be attached to the peritoneum through the application of an adhesive between the film and peritoneum, or by fixation of the film to the peritoneum by suturing, stapling, and the like.

As shown in FIG. 3C, upon attachment of the film to the peritoneum, the balloon 302 may be deflated via the inflating/deflating means 328. For example, the previously supplied inflation fluid (e.g., $CO_2$, air, saline or the other fluid) may be withdrawn from the balloon to deflate the balloon. As shown in this figure, when the balloon is deflated, the film remains attached to the peritoneum. The balloon may then be retracted from the cannula 320 (see arrow Z), leaving the protective film 304 attached to the peritoneum. The deployed film may then enhance the integrity of the peritoneum and minimize or even eliminate the occurrence of shredding, tearing, or puncturing during the surgical procedure.

Figure 4A:
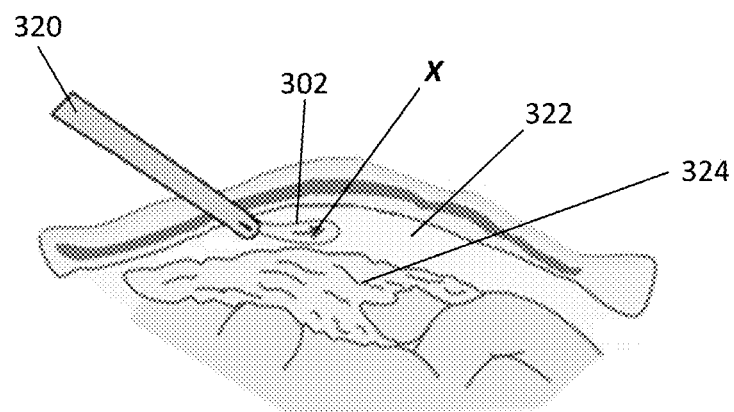
FIGS. 4A-4C illustrate a method of applying a protective lining to a peritoneum according to another embodiment.
Figure 4B:
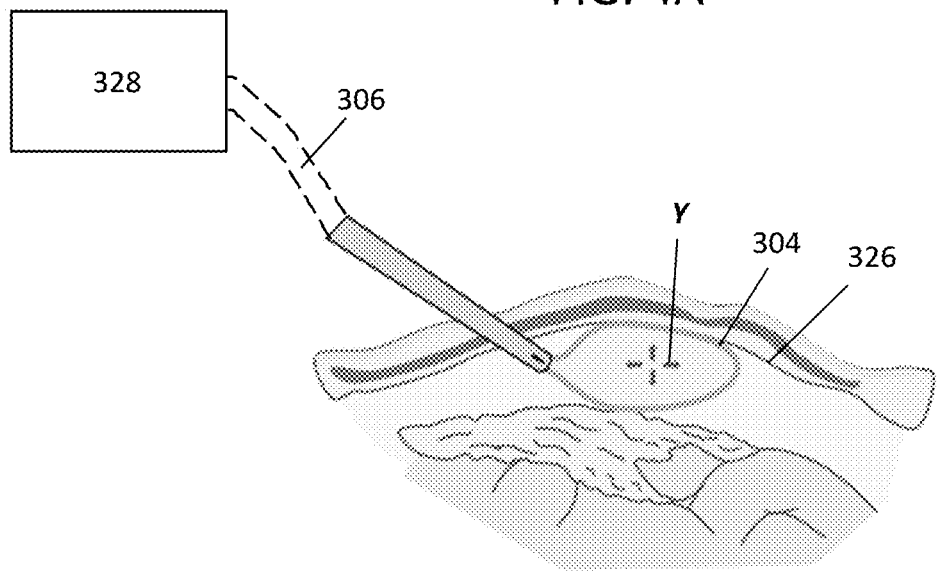
Figure 4C:
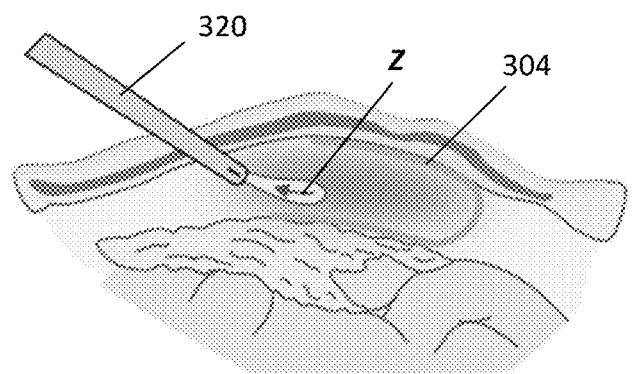

Although the method described in FIGS. 3A-3C includes first insufflating the abdominal cavity before inserting and inflating the film-covered balloon, in other embodiments, the film-covered balloon may be used to both insufflate the abdominal cavity and deliver the protective film. For example, as shown in FIG. 4A, after inserting the cannula 320, a deflated, film-covered balloon 302 may be inserted into the abdominal cavity (see arrow X). As with other embodiments, as shown in FIG. 4B, the balloon 32 may be inflated (see arrows Y) via the inflating/deflating means 328. Such inflation may be used to both elevate the abdominal wall, including the peritoneum, away from the viscera, and also place the film in contact with the peritoneum. After inflation, the balloon may be deflated via the inflation/deflation means, with the film remaining attached to the peritoneum, and the balloon may be retracted (see FIG. 4C).

Figure 5A:
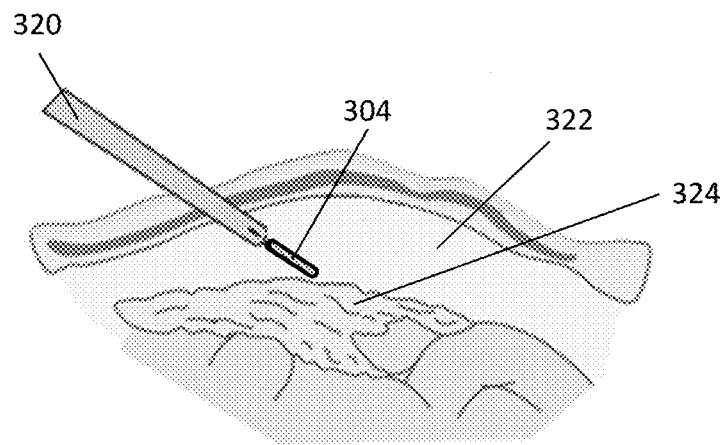
FIGS. 5A-5C illustrate a method of applying a protective lining to a peritoneum according to yet another embodiment.
Figure 5B:
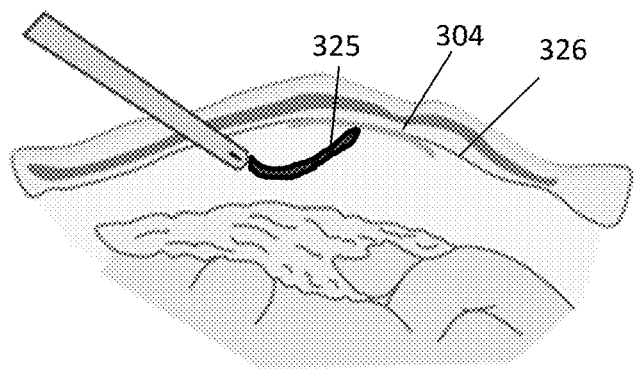
Figure 5C:
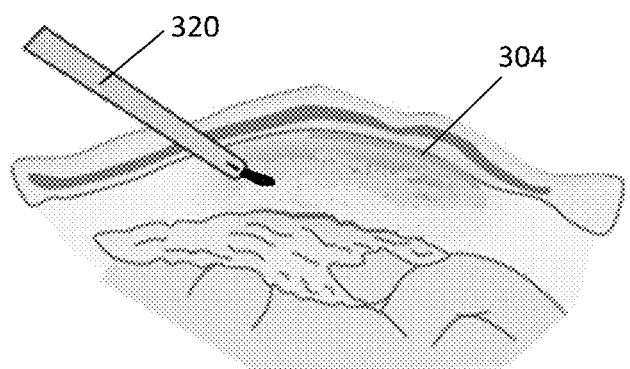

FIGS. 5A-5C illustrate another example by which a pre-formed film may be applied to the peritoneum. As with other embodiments, the abdominal wall, including the peritoneum, is elevated away from the viscera and a cannula 320 extends from outside of the patient, through the abdominal wall, and into the abdominal cavity 322. As shown in FIG. 5A, a rolled up film 304 may be delivered to the abdominal cavity via the cannula 320. Next, a surgical tool 325, such as a grasper, may be used to unroll the film and position the film against the peritoneum, such as for attachment. As with other embodiments, the film may be inherently tacky, include an adhesive, or otherwise be composed so as to adhere to the peritoneum. Once the film 304 is attached, the surgical tool may be retracted via the cannula.

Although only a single pre-formed film is shown as being applied to the peritoneum via the methods illustrated in FIGS. 3A-3C, 4A-4C, and 5A-5C, in other embodiments, additional films may be applied to the peritoneum. In some embodiments, the additional films are applied on top of the first film attached to the peritoneum. For example, a second balloon may be inserted into the expanded body cavity and inflated to attach a second film to the first film on the peritoneum. In other embodiments, the additional films are applied to other regions of the peritoneum. For example, a rolled up film may be introduced into the cannula, with a grasper or other surgical tool used to unroll the film and position the film against a second, unprotected portion of the peritoneum for attachment.

Figure 6A:
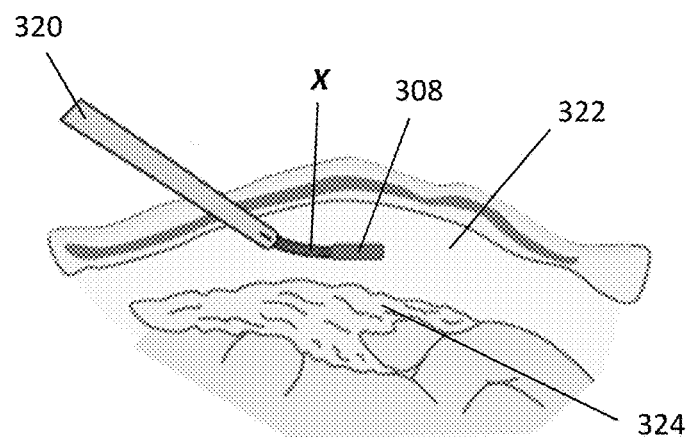
FIGS. 6A-6C illustrate a method of applying a protective lining to a peritoneum according to still another embodiment.
Figure 6B:
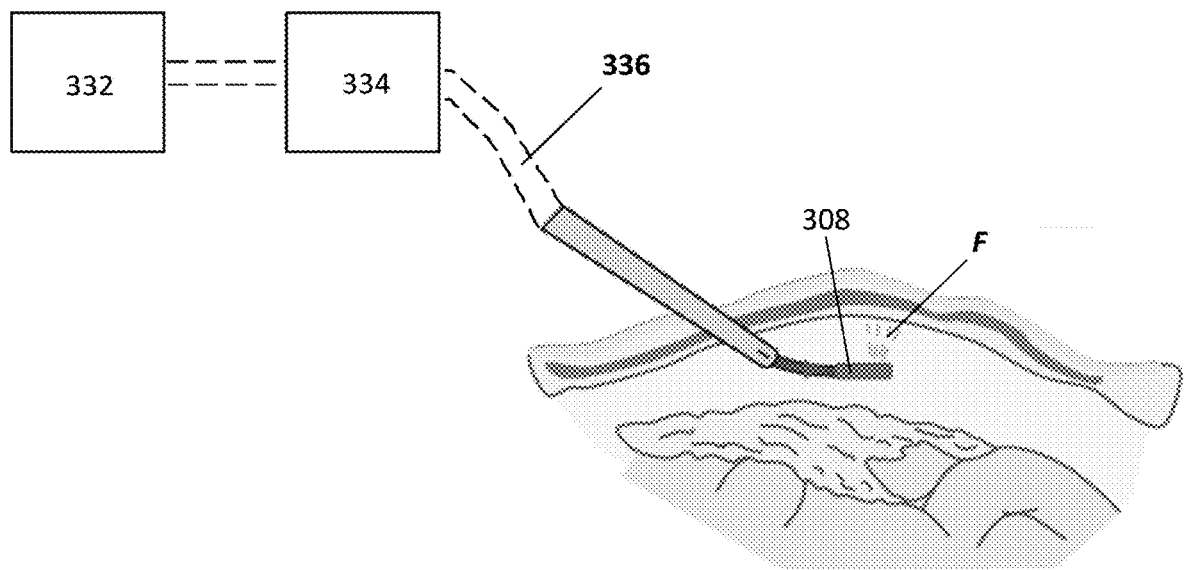
Figure 6C:
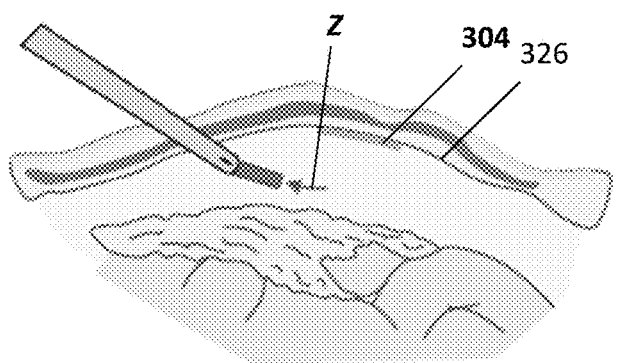

FIGS. 6A-6C illustrate another method of applying a protective lining to the peritoneum. Here, again, the abdominal wall, including the peritoneum, is elevated away from the viscera such as by introduction of an insufflation gas. As shown in FIGS. 6A-6B, an instrument for spraying a protective lining is then introduced through the cannula 320 (see arrow X) and positioned to apply a sprayable film over at least a portion of the peritoneum (see arrows F) desired to be protected. In some embodiments, the film is applied using pressurized gas supplied via a gas supply 332. In such embodiments, the pressurized gas acts as a propellant to distribute the sprayable film, stored in a fluid chamber 334, to the desired area of the peritoneum (e.g., via a conduit 336 connected to a nozzle 308). Although the sprayable film is shown as being stored in a fluid chamber connectable to the nozzle, the sprayable film also may be stored in a reservoir within the flexible nozzle in other embodiments. As shown in FIG. 6C, after application of the protective lining to the peritoneum, the instrument may then be retracted from the body cavity (see arrow Z).

As will be appreciated, in some embodiments, only a single layer of sprayable film may be applied to an area of the peritoneum before removing the flexible nozzle from the body cavity. In other embodiments, after a first layer of film is applied to the peritoneum, a second layer of film may be applied to the peritoneum. As with other embodiments, the second layer of film may be applied on top of the first layer of film. The second layer of film also may be applied to a second, different area of the peritoneum. As will be further appreciated, additional layers, such as third or fourth layers also may be applied to the peritoneum.

In some embodiments, application of the film (e.g., either via the balloon or via the flexible nozzle) may be accomplished with a surgical instrument that is manipulated by a surgeon. For example, the surgeon may manually direct the balloon or flexible nozzle through the cannula and into the body cavity to apply the protective lining to the peritoneum. In other embodiments, application of the lining may be accomplished during a robot-assisted surgery. In such embodiments, a surgeon may direct one or more mechanical arms with attached surgical instruments. For example, the surgeon may direct a robotic arm with an inflatable balloon to pass the balloon into the body cavity (via the cannula), inflate the balloon to make contact between the lining and the surrounding tissue, and deflate and retract the balloon from the body cavity once the lining has been attached the peritoneum.

Figure 7:
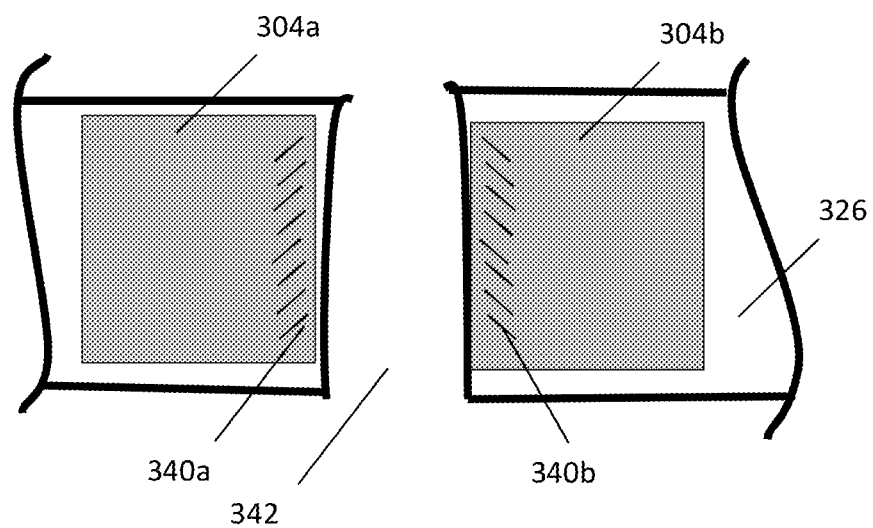
FIG. 7 is a bottom view of a peritoneum with two attached protective linings.

In some embodiments, the protective film also may be arranged to facilitate closure of the peritoneum. For example, as shown in FIG. 7, a first protective film 304a attached to the peritoneum 326 may include a first fixation element 340a engageable with a corresponding second fixation element 340b on a second protective film 304b attached to the peritoneum 326. As shown in this view, the first film and first fixation element are positioned on a first side of an opening 342 of the peritoneum and the second film and second fixation element are positioned on a second, opposite side of the opening. In some embodiments, the fixation elements may be mechanically engaged with one another. For example, the first protective film may include hooks that engage with corresponding loops on the second protective film. Once the fixation elements are engaged, the first and second films may be attached to one another, thus closing the opening 342 in the peritoneum. Other arrangements also may be used to facilitate closure of the peritoneum. For example, the first and second protective layers may have loops through which sutures may be passed through to pull the layers together and close the peritoneum.

Although the apparatuses and methods have been described for protecting the peritoneum during a surgical procedure, it will be appreciated that such techniques may be used to prophylactically prevent shredding or other injury to other tissues in the body that are exposed during a surgical procedure. Additionally, although embodiments involving a balloon and a nozzle have been described for applying the protective film to the tissue, it will be appreciated that other application methods may be used to apply the film prior to a surgical procedure.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method of applying a protective lining to a peritoneum, the method comprising:
    elevating an abdominal wall including a peritoneum away from viscera to create a working space;
    performing an active surgical intervention involving the created working space, wherein the active surgical intervention is selected from the group consisting of: a preperitoneal hernia repair, an intraperitoneal hernia repair, a cholecystectomy, an appendectomy, splenectomy, and a nephrectomy; and
    prior to the act of performing an active surgical intervention, applying a protective lining to at least a portion of the peritoneum in the working space to prophylactically prevent shredding, tearing, or other injury to the peritoneum, protect and/or preserve the fidelity of the peritoneum, add stability to the peritoneum, and/or facilitate incision formation and/or closure of the peritoneum, the protective lining being attachable to the peritoneum and remaining attached to the peritoneum after the active surgical intervention to minimize or prevent post-operative adhesion and/or prevent discomfort.

2. The method of claim 1, wherein the act of applying a protective lining includes applying a pre-formed protective lining to the at least a portion of the peritoneum.

3. The method of claim 2, wherein the act of applying a pre-formed protective lining includes providing the pre-formed protective lining on an expandable delivery device.

4. The method of claim 3, wherein the expandable delivery device includes an expandable balloon.

5. The method of claim 4, wherein the act of applying the pre-formed protective lining includes inflating the balloon such that the pre-formed protective lining contacts the at least a portion of the peritoneum.

6. The method of claim 4, wherein the step of elevating the abdominal wall includes elevating the abdominal wall via the expandable delivery device.

7. The method of claim 2, wherein the pre-formed protective lining includes a transferable film.

8. The method of claim 7, wherein the transferable film includes an adhesive to attach the transferable film to the peritoneum.

9. The method of claim 8, wherein the adhesive is moisture activated.

10. The method of claim 7, wherein the transferable film includes one or more clips or tacks to attach the transferrable film to the peritoneum.

11. The method of claim 2, wherein the act of applying a pre-formed protective lining includes inserting a rolled up pre-formed lining into the working space via a cannula.

12. The method of claim 11, wherein the act of applying a pre-formed protective lining includes unrolling the pre-formed lining via a surgical tool.

13. The method of claim 12, wherein the act of applying a pre-formed protective lining includes positioning the unrolled pre-formed lining against the at least a portion of the peritoneum via the surgical tool.

14. The method of claim 13, wherein the act of applying a pre-formed protective lining includes attaching the unrolled pre-formed lining to the peritoneum.

15. The method of claim 1, wherein the act of applying a protective lining includes spraying a protective lining onto the at least a portion of the peritoneum.

16. The method of claim 15, wherein the act of spraying a protective lining includes inserting a nozzle portion of an instrument for spraying into the created working space.

17. The method of claim 1, wherein the act of applying the protective lining includes applying a first layer of a protective lining onto the at least a portion of the peritoneum and then applying a second layer of a protective lining onto the first layer.

18. The method of claim 1, wherein the act of applying the protective lining includes applying a first layer of a protective lining onto a first region of the at least a portion of the peritoneum and then applying a second layer of a protective lining onto a second region of the at least a portion of the peritoneum.

19. The method of claim 18, further comprising engaging a first fixation element on the first layer with a second fixation element on the second layer to close an opening in the peritoneum.

20. The method of claim 19, wherein the first layer is positioned on a first side of the opening and the second layer is positioned on a second side, wherein the first and second fixation elements are engageable to attach the first and second layers to one another.

21. The method of claim 1, wherein the active surgical intervention is a laparoscopic procedure or a robotic assisted surgical procedure.

22. The method of claim 1, wherein the act of applying a protective lining includes applying the protective lining prior to the act of elevating the abdominal wall.

23. The method of claim 1, wherein the protective lining is arranged to resemble native peritoneum tissue.

24. A method of applying a protective lining to a peritoneum, the method comprising:
    elevating an abdominal wall including a peritoneum away from viscera to create a working space;
    performing an active surgical intervention involving the created working space; and
    prior to the act of performing an active surgical intervention, applying a protective lining to at least a portion of the peritoneum in the working space, the protective lining being attachable to the peritoneum;
    wherein the act of applying a protective lining includes applying a pre-formed protective lining to the at least a portion of the peritoneum, the pre-formed protective lining including a transferable film having an adhesive to attach the transferable film to the peritoneum, the adhesive being moisture activated;
    wherein the pre-formed protective lining is arranged to remain attached to the peritoneum after the active surgical intervention to minimize or prevent post-operative adhesion and/or prevent discomfort.

25. The method of claim 24, wherein the step of elevating the abdominal wall includes elevating the abdominal wall via an expandable balloon.

26. The method of claim 24, wherein the act of applying the pre-formed protective lining includes applying the protective lining prior to the act of elevating the abdominal wall.

27. The method of claim 24, wherein the protective lining is arranged to resemble native peritoneum tissue.

28. The method of claim 24, wherein the active surgical intervention is a laparoscopic procedure or a robotic assisted surgical procedure.

29. A method of applying a protective lining to a peritoneum, the method comprising:
   elevating an abdominal wall including a peritoneum away from viscera to create a working space;
   performing an active surgical intervention involving the created working space, wherein the active surgical intervention is selected from the group consisting of: a preperitoneal hernia repair, an intraperitoneal hernia repair, a cholecystectomy, an appendectomy, a splenectomy, and a nephrectomy; and
   prior to the act of performing an active surgical intervention, applying a protective lining to at least a portion of the peritoneum in the working space via an expandable balloon, the protective lining being attachable to the peritoneum and remaining attached to the peritoneum after removal of the expandable balloon and after the active surgical intervention.

30. The method of claim 29, wherein the act of applying the protective lining includes applying a pre-formed protective lining to the at least a portion of the peritoneum.

31. The method of claim 30, wherein the pre-formed protective lining includes a transferable film.

32. The method of claim 29, wherein the act of applying the protective lining includes inflating the expandable balloon such that a pre-formed protective lining contacts the at least a portion of the peritoneum.

33. The method of claim 29, wherein the step of elevating the abdominal wall includes elevating the abdominal wall via the expandable balloon.

34. The method of claim 29, wherein the protective lining is arranged to resemble native peritoneum tissue.

* * * * *